(12) United States Patent
Ghelli et al.

(10) Patent No.: US 11,732,726 B2
(45) Date of Patent: Aug. 22, 2023

(54) MAGNETIC LEVITATION CENTRIFUGAL PUMP

(71) Applicant: EUROSETS S.R.L., Medolla (IT)

(72) Inventors: Nicola Ghelli, Medolla (IT); Paolo Fontanili, Medolla (IT); Edgardo Costa Maianti, Medolla (IT)

(73) Assignee: EUROSETS S.R.L., Medolla (IT)

( * ) Notice: Subject to any disclaimer, the term of this patent is extended or adjusted under 35 U.S.C. 154(b) by 121 days.

(21) Appl. No.: 17/285,071

(22) PCT Filed: Oct. 16, 2019

(86) PCT No.: PCT/IB2019/058809
§ 371 (c)(1),
(2) Date: Apr. 13, 2021

(87) PCT Pub. No.: WO2020/079603
PCT Pub. Date: Apr. 23, 2020

(65) Prior Publication Data
US 2022/0025896 A1 Jan. 27, 2022

(30) Foreign Application Priority Data
Oct. 16, 2018 (IT) .................... IT102018000009502

(51) Int. Cl.
*F04D 29/048* (2006.01)
*F04D 13/02* (2006.01)
(Continued)

(52) U.S. Cl.
CPC ......... *F04D 29/048* (2013.01); *A61M 60/104* (2021.01); *A61M 60/232* (2021.01);
(Continued)

(58) Field of Classification Search
CPC .............. F04D 13/025; F04D 13/0606; F04D 13/0626; F04D 29/426; F04D 29/4293;
(Continued)

(56) References Cited

U.S. PATENT DOCUMENTS 5,803,720 A * 9/1998 Ohara ................. A61M 60/825
415/206
2006/0222533 A1* 10/2006 Reeves ............... A61M 60/531
417/423.1
(Continued)

FOREIGN PATENT DOCUMENTS

| GB | 1383811 A | 2/1974 |
|---|---|---|
| GB | 2177466 A | 1/1987 |
| JP | 2015084792 A | 5/2015 |

*Primary Examiner* — Kenneth J Hansen
(74) *Attorney, Agent, or Firm* — Aslan Law, P.C.

(57) ABSTRACT

A magnetic levitation centrifugal pump comprises: an internally hollow body, an inlet connector and an outlet connector for blood. The hollow body comprises a lower element and an upper element which are mutually coupled to each other; a rotor element housed inside the hollow body and provided with a portion made of magnetic material, the rotor element being magnetically commanded in rotation about a relative axis, without contact, by a stator element associable with the hollow body. The upper element has a perimeter flange for coupling and a substantially dome-shaped body projecting from the perimeter flange. The outlet connector is associated with the dome-shaped body and is spaced away from the perimeter flange, between the outlet connector and the perimeter flange being defined an air space inside which mutual tightening device/component can be inserted for the tightening of the upper element with the lower element.

3 Claims, 3 Drawing Sheets

(51) Int. Cl.
  *F04D 13/06*    (2006.01)
  *F04D 29/42*    (2006.01)
  *A61M 60/806*   (2021.01)
  *A61M 60/827*   (2021.01)
  *A61M 60/104*   (2021.01)
  *A61M 60/81*    (2021.01)
  *A61M 60/422*   (2021.01)
  *A61M 60/232*   (2021.01)

(52) U.S. Cl.
  CPC ........ *A61M 60/422* (2021.01); *A61M 60/806* (2021.01); *A61M 60/81* (2021.01); *A61M 60/827* (2021.01); *F04D 13/025* (2013.01); *F04D 13/0626* (2013.01); *F04D 29/4293* (2013.01)

(58) Field of Classification Search
  CPC ... A61M 60/104; A61M 60/232; A61M 60/81
  See application file for complete search history.

(56) References Cited

U.S. PATENT DOCUMENTS

| | | | |
|---|---|---|---|
| 2014/0017073 A1* | 1/2014 | Muizelaar | F04D 13/0606 415/177 |
| 2017/0146030 A1 | 5/2017 | Furukawa | |
| 2017/0361001 A1* | 12/2017 | Canatella | A61M 60/857 |

* cited by examiner

MAGNETIC LEVITATION CENTRIFUGAL PUMP

CROSS-REFERENCE TO RELATED APPLICATIONS

This application claims priority to IT Patent Application No. 102018000009502 filed on Oct. 16, 2018, and this application claims priority to and is a 371 of international PCT Application No. PCT/IB2019/058809 filed on Oct. 16, 2019, the entire contents of which are hereby incorporated by reference.

TECHNICAL FIELD

The present invention relates to a magnetic levitation centrifugal pump.

BACKGROUND ART

The magnetic levitation centrifugal pumps used in the biomedical sector are generally composed of an internally hollow body, provided with at least one blood inlet connector and one blood outlet connector, inside which is housed a rotor element provided with a plurality of blades adapted to convey, as a result of the rotation of the rotor element itself, the incoming blood towards the outlet connector.

The rotor element comprises a portion of magnetic material, and outside the hollow body a stator element is positioned which is adapted to define at least one magnetic field for lifting and controlling the rotor element in rotation inside the hollow body.

More particularly, the hollow body is generally composed of two or more elements coupled together, of which at least one is the upper element and one is the lower element.

The upper element has a perimeter flange for coupling with the lower element, from which flange a dome-shaped portion extends, adapted to house the rotor element.

The perimeter flange defines a coupling surface that is locked together with the lower element, e.g. by welding, and where a sealing element, e.g. of the type of an O-ring, is positioned between this coupling surface and the lower element.

In the pumps of known type, the blood inlet connector is positioned at the point where the dome-shaped portion is located and the outlet connector, placed at a lower level than the inlet connector, is positioned at the point where the perimeter flange is located.

The outlet connector of the pumps of known type is therefore located substantially tangential to the perimeter flange.

In some solutions of known type, the outlet connector is partly defined on the upper element and partly on the lower element.

These centrifugal pumps of known type do have some drawbacks.

In fact, the positioning of the outlet connector means that the coupling surface features several discontinuities, which make the mutual welding of the contact parts difficult.

The presence of the outlet connector at the point where the perimeter flange is located also makes it difficult to keep the lower element in contact with the coupling surface during the welding phase.

In addition, the irregularities in the coupling surface cause the O-ring positioned between the coupling surface and the lower element to lead to the formation of blood stagnation cavities and/or protrusions that may damage blood.

Yet another drawback consists in the fact that during the welding phase, which is generally carried out by ultrasound, dust develops which may enter the area intended for the treatment of blood, contaminating it.

Some centrifugal pumps of known type are described by JP 2015 084792 A and by US 2017/363103 A, both of which having a relevant outlet connector located tangentially to the perimeter flange.

DESCRIPTION OF THE INVENTION

The main aim of the present invention is to devise a magnetic levitation centrifugal pump that allows simplifying, compared to the solutions known to date, the coupling between the upper element and the lower element that make up the hollow body inside which the rotor element is housed.

Within this aim, one object of the present invention is to facilitate the maintenance of contact of the perimeter flange with the lower element during the welding operations.

Another object of the present invention is to facilitate, and at the same time to make less dangerous for the treated blood, the positioning of the sealing means positioned between the upper element and the lower element.

Not the last object of the present invention is to reduce the risk that the dust generated by the welding operation for the locking of the upper element together with the lower element enters the area designated for the treatment of blood.

Another object of the present invention is to devise a magnetic levitation centrifugal pump which allows overcoming the aforementioned drawbacks of the prior art in a simple, rational, easy, effective to use and low cost solution.

The aforementioned objects are achieved by the present magnetic levitation centrifugal pump according to claim 1.

BRIEF DESCRIPTION OF THE DRAWINGS

Other characteristics and advantages of the present invention will be more evident from the description of a preferred, but not exclusive, embodiment of a magnetic levitation centrifugal pump, illustrated by way of a non-limiting example in the accompanying tables of drawing in which.

EMBODIMENTS OF THE INVENTION

Figure 1:
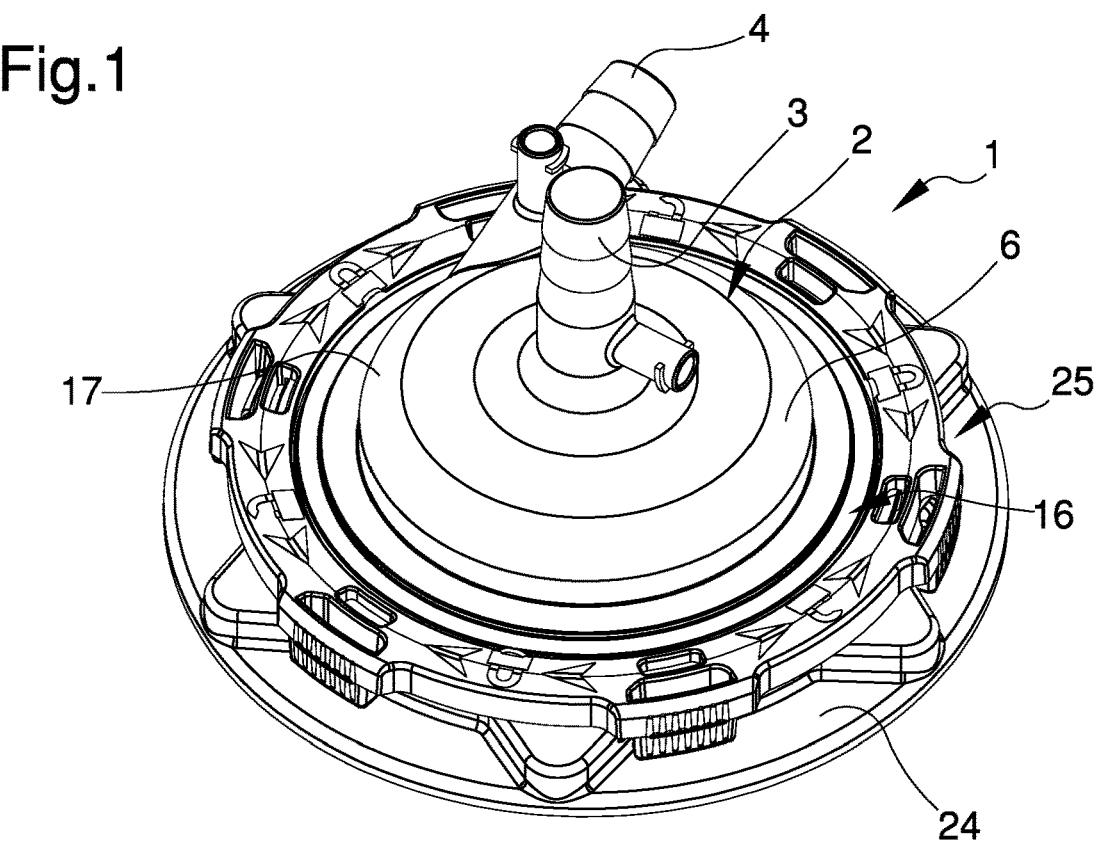
FIG. 1 is an axonometric view of a pump according to the invention.

With particular reference to these illustrations, reference numeral 1 globally indicates a magnetic levitation centrifugal pump.

The pump 1 comprises at least one internally hollow body 2 provided with at least one inlet connector 3 for the venous blood coming from a patient and with at least one outlet connector 4 for the venous blood to be conveyed to a blood oxygenation device.

The hollow body 2 comprises at least one lower element 5 and at least one upper element 6 which are separated and mutually coupled to each other.

The hollow body 2 defines therefore a volume 7, on which the inlet connector 3 and the outlet connector 4 face, inside which is housed at least one rotor element 8 provided with at least one portion made of magnetic material, identified in the figures with reference number 9.

The rotor element 8 can be magnetically commanded in rotation about a relative axis X, without contact, by a stator element (not shown in the illustrations), associable with the hollow body 2 and adapted to generate a magnetic field.

In the attached figures are also shown, although not part of the present invention, the covering element 24 of the stator element mentioned above, which is intended to support the hollow body 2 and the anchoring element 25 of the hollow body 2 to the covering element 24.

The way in which the rotation of the rotor element 8 is controlled, although not related to in the present invention, is widely known to the technician in the field.

In particular, the stator element comprises a plurality of windings intended to be crossed by the electric current for the formation of one or more magnetic fields which are adapted to interact with the rotor element 8 to raise and bring it in rotation around the relevant axis X.

More particularly, the rotor element 8 comprises a revolving body 10, provided with a plurality of blades 11 arranged in a radial pattern thereon and adapted to contact the blood entering the volume 7 to push it towards the outlet connector 4.

Advantageously, the revolving body 10 has a contact surface 26, facing upwardly during use, having a concave shape. More in detail, the contact surface 26 has a substantially curvilinear extension so as to accompany the flow of blood in its drop inside the volume 7 through the inlet duct 3, so as to reduce the risk of damage due to the impact with the revolving body itself.

The revolving body 10 is also provided with a housing seat 12, defined at its bottom portion, inside which the magnetic portion 9 is inserted, closed at the bottom by a retaining element 13.

In addition, the lower element 5 has a housing 14 adapted to contain, in use, at least one portion of the revolving body 10, the blades 11 remaining outside the housing itself, which has a bottom wall 14a provided with a guiding element 14b, defined at the axis of rotation X, for the centering of the rotor element 8. More in detail, the revolving body 10 has a sleeve 10a that is inserted into the relevant holes 15 formed in the magnetic portion 9 and in the retaining element 13; following the insertion of the rotor element 8 inside the housing 14, the lower end of the sleeve 10a is fitted on the guiding element 14b coaxially to the axis of rotation X.

According to the invention, the upper element 6 has at least one perimeter flange 16 for coupling to the lower element 5 and at least one substantially dome-shaped body, identified in the illustrations with the reference numeral 17, which protrudes from the perimeter flange 16, where the outlet connector 4 is associated with the dome-shaped body 17 and is spaced away from the perimeter flange 16. Between the outlet connector 4 and the perimeter flange 16, an air space 18 is defined inside which mutual tightening means can be inserted for the tightening of the upper element 6 with the lower element 5.

Appropriately, the perimeter flange 16 defines at least one abutment surface 28a which is intended to rest on the covering element 24 and which corresponds to one end surface of the hollow body 2. In other words, the abutment surface 28a defines one end, and in particular the lower end when using the pump 1, of the hollow body 2.

The perimeter flange 16 then defines at least one holding surface 28b opposite the abutment surface 28a, which is spaced away from the outlet connector 4. The air space 18 is then positioned between the holding surface 28b and the outlet connector 4.

Advantageously, the perimeter flange 16 defines at least one coupling surface 16a with the lower element 5 and the outlet connector 4 is raised with respect to the coupling surface 16a.

Preferably, the coupling surface 16a is substantially flat.

In the embodiment shown in the figures, the coupling surface 16a and the abutment surface 28a are arranged on the same side, where the coupling surface 16a is arranged internally with respect to the abutment surface 28a.

More in detail, the perimeter flange 16 defines at least one top surface 16b opposite the coupling surface 16a and the outlet connector 4 is spaced away from the top surface itself. The air space 18 is therefore also defined between the top surface 16b and the outlet connector 4.

The top surface 16b is the one from which the dome-shaped body 17 extends.

The top surface 16b is positioned on the same side as the holding surface 28b, internally with respect thereto. In the embodiment shown in the illustrations, the top surface 16b is arranged staggered with respect to the holding surface 28b. In particular, in use, the top surface 16b is arranged at a higher level than the holding surface 28b.

Appropriately, sealing means 19, e.g. of the type of an O-ring, are placed between the coupling surface 16a and the lower element 5.

Figure 2:
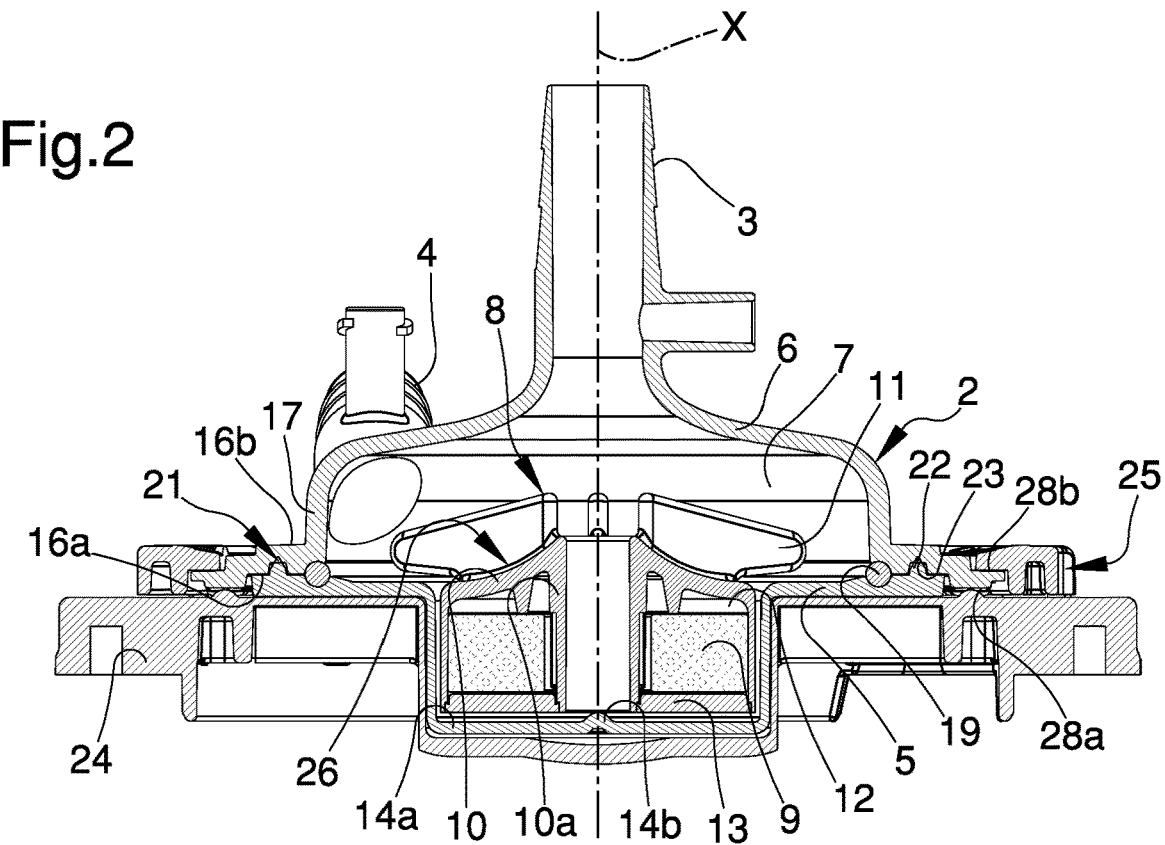
FIG. 2 is a first cross-sectional view of the pump in FIG. 1.
Figure 3:
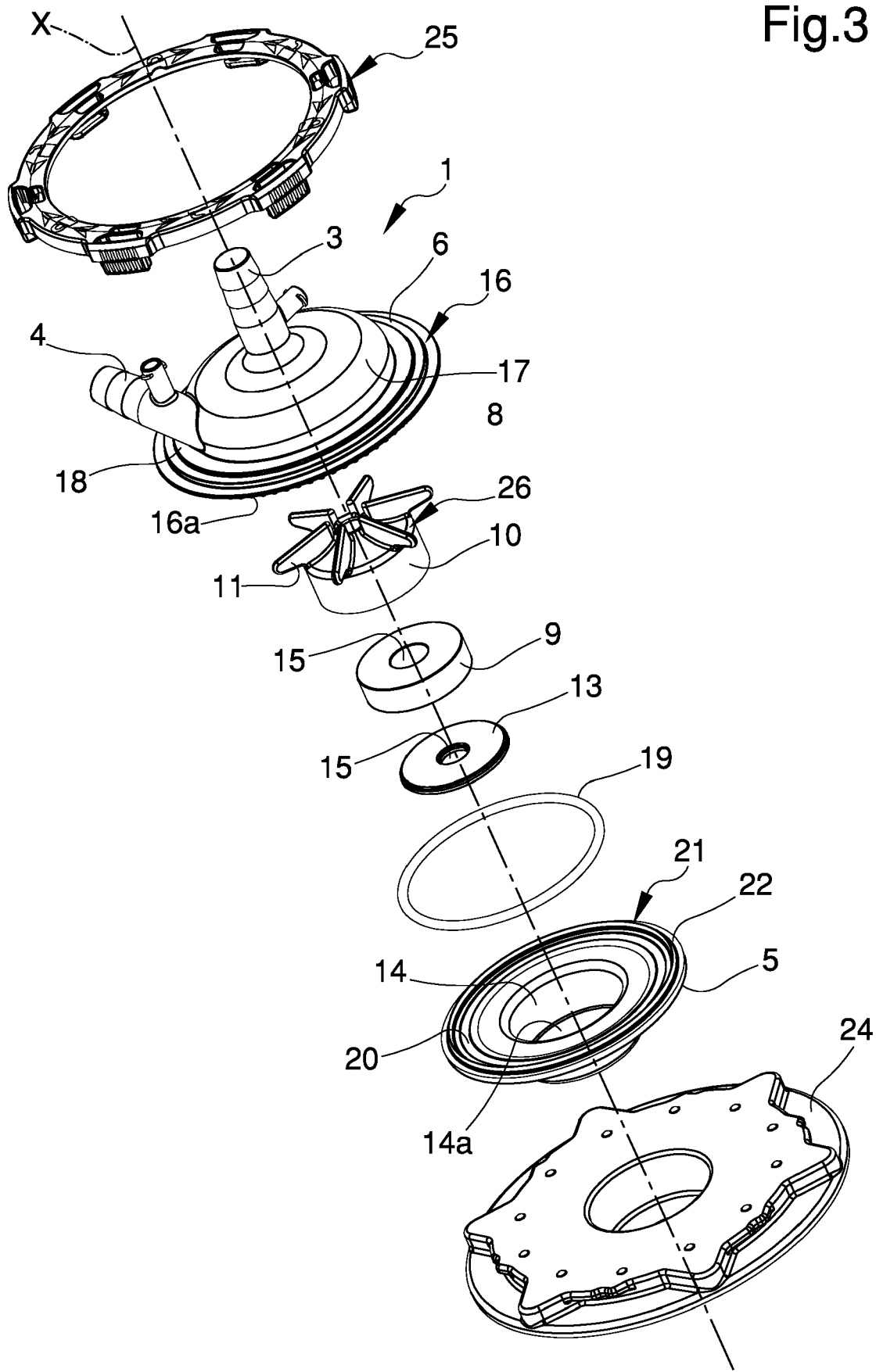
FIG. 3 is an exploded view of the pump in FIG. 1.
Figure 4:
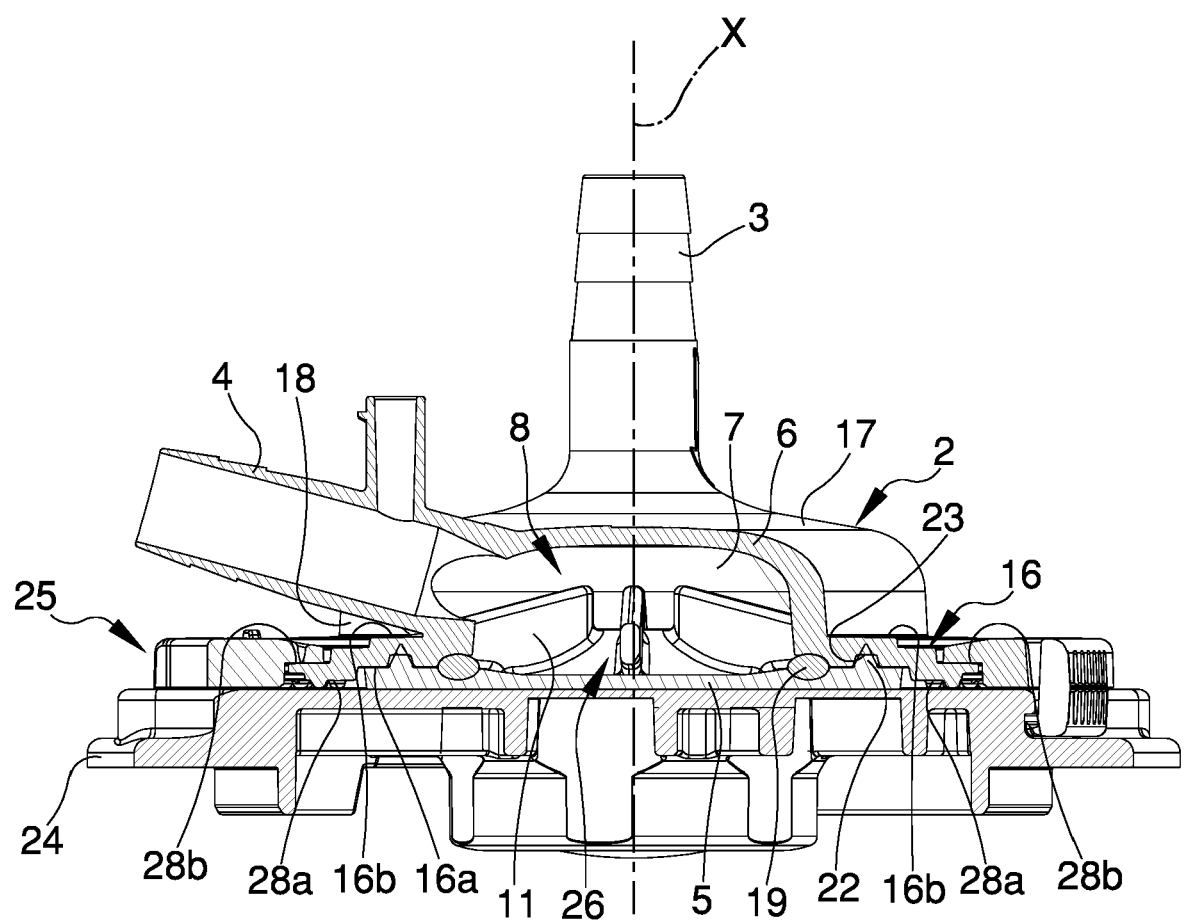
FIG. 4 is a second cross-sectional view of the pump in FIG. 1.

More particularly, as shown in FIG. 2, the O-ring 19 is placed at the inner edge of the coupling surface 16a and faces the volume 7 inside the hollow body 2.

The lower element 5 also comprises a groove 20 adapted to house the O-ring 19 to prevent it from moving during use.

Preferably, the outlet connector 4 is oriented transversely with respect to the axis of rotation X.

More in detail, the elongated outlet connector 4 is inclined with respect to the coupling surface 16a. The outlet connector 4 is also inclined with respect to a plane passing through the axis of rotation X. In other words, the outlet connector 4 is inclined with respect to the inlet connector 3, i.e. with respect to a plane passing through the axis of rotation X, by an angle of less than 90°.

In the preferred embodiment shown in the figures, the inlet connector 3 is positioned at the top of the upper element 6 and extends coaxially to the axis of rotation X.

Conveniently, the upper element 6 and the lower element 5 are provided with relevant centering means 21 adapted to ensure their correct mutual positioning.

More in detail, the centering means 21 comprise at least one relief 22 defined on one of either the coupling surface 16a or the lower element 5 and at least one recess 23 defined on the other of either the lower element 5 or the coupling surface 16a, where the relief 22 is adapted to be inserted in the recess 23 following the positioning of the upper element 6 on the lower element 5.

Since in the preferred embodiment shown in the illustrations, the upper element 6 and the lower element 5 have a substantially circular section, the recess 23 and the relief 22 have a substantially annular extension.

The centering means 21, and in particular the relief 22 and the recess 23, can be used as sealing means as a result of their mutual locking, e.g. by means of welding and/or gluing. The relief 22 and the recess 23 can therefore give the mechanical and/or hydraulic seal in the coupling between the lower element 5 and the upper element 6.

The sealing means may therefore comprise at least one of either the O-ring 19 and the centering means 21, or preferably both.

Appropriately, the centering means 21 are arranged downstream of the O-ring 19 proceeding from the volume 7 outwards.

The assembly of the magnetic levitation centrifugal pump according to the present invention is as follows.

Initially, the magnetic portion 9 is inserted into the housing seat 12 and the latter is closed with the retaining element 13, so that the sleeve 10a passes through the holes 15.

The rotor element 8 obtained this way is then positioned inside the housing 14 in such a way as to fit the open end of the sleeve 10a on the guiding element 10b.

Subsequently, the O-ring 19 is positioned inside the groove 20 and the upper element 6 is applied on top of it so that the relief 22 defined on the lower element 5 is inserted inside the recess 23 defined at the point where the coupling surface 16a is located.

Once the upper element 6 has been coupled to the lower element 5, they are locked together, e.g. by welding, at the point where the coupling surface 16a is located.

The upper element 6 and the lower element 5 can be kept in contact with each other during the welding operation, e.g. by means of tightening means applied at the perimeter coupling flange 16, without interfering with the outlet connector 4 of the blood.

It has in practice been ascertained that the described invention achieves the intended objects and, in particular, the fact is underlined that the positioning of the outlet connector in a separate area from the perimeter coupling flange of the upper element to the lower element allows defining a substantially flat coupling surface, thus facilitating the correct positioning thereof with the lower element. This positioning of the outlet connector also allows the upper element to be kept in contact with the lower element in the correct position during the welding operation.

Furthermore, the pump, which the present invention relates to, makes it possible to simplify, compared to known pumps, the positioning of the sealing means between the upper element and the lower element, in such a way that they face directly the internal volume, thus avoiding the formation of blood stagnation areas or protrusions which could damage the same.

The invention claimed is:

1. A magnetic levitation centrifugal pump comprising:
   at least one internally hollow body provided with at least one inlet connector and with at least one outlet connector for blood, where said at least one internally hollow body comprises at least one lower element and at least one upper element which are mutually coupled to each other;
   at least one rotor element housed inside said at least one internally hollow body and provided with at least one portion made of magnetic material, said at least one rotor element being magnetically commanded in rotation about an axis of rotation, without contact, by a stator element associable with said at least one internally hollow body, wherein
   said at least one upper element has at least one perimeter flange for coupling and at least one substantially dome-shaped body projecting from said at least one perimeter flange,
   said at least one outlet connector is associated with said at least one substantially dome-shaped body and is spaced away from said at least one perimeter flange, so that an air space is defined between said at least one outlet connector and said at least one perimeter flange,
   said at least one outlet connector is spaced in a direction vertically or axially away from said at least one perimeter flange,
   said at least one perimeter flange defines at least one coupling surface with said at least one lower element, said at least one outlet connector spaced axially upward from said at least one coupling surface,
   said at least one coupling surface is substantially flat,
   said at least one perimeter flange defines at least one top surface opposite said at least one coupling surface,
   said at least one outlet connector is spaced away from said at least one top surface,
   said at least one substantially dome-shaped body extends from said at least one top surface,
   said air space is defined between said at least one top surface and said at least one outlet connector,
   said at least one perimeter flange defines at least one abutment surface, supported by a covering element of the stator element and turned to the same side as said at least one coupling surface, and at least one holding surface, opposite said at least one abutment surface and spaced away from said at least one outlet connector, said air space being positioned between said at least one holding surface and said at least one outlet connector,
   said at least one coupling surface and said at least one top surface are arranged radially inward of said at least one abutment surface and to said at least one holding surface, respectively, and
   said at least one top surface is arranged on the sane side as said at least one holding surface and is staggered with respect thereto;
   sealing means placed between said at least one coupling surface and said at least one lower element, wherein
   said sealing means comprise at least one O-ring, the at least one O-ring faces said at least one internally hollow body in a radially inward direction,
   said at least one outlet connector is oriented transversely with respect to said axis of rotation,
   said at least one outlet connector is inclined with respect to said at least one coupling surface,
   said at least one outlet connector is inclined with respect to said axis of rotation ban angle of less than 90°,
   said at least one upper element and said at least one lower element are provided with corresponding centering means which are adapted to ensure their correct mutual positioning,
   said centering means comprise at least one relief defined on one of either said at least one coupling surface or said at least one lower element and at least one recess defined on the other of either said at least one lower element or said at least one coupling surface, where said at least one relief is adapted to be inserted in said at least one recess following the coupling of said at least one upper element to said at least one lower element,
   said at least one relief and said at least one recess are adapted to be locked together and are adapted to define said sealing means, and
   said centering means are arranged downstream of said O-ring in a radial direction with respect to said at least one internally hollow body outwards.

2. The magnetic levitation centrifugal pump according to claim 1, wherein
   said at least one rotor element comprises a revolving body, provided with a plurality of blades which are adapted to contact the blood entering said at least one inlet connector to push it towards said at least one outlet connector, where said revolving body has a contact surface, facing upwardly during use, having a concave shape.

3. The magnetic levitation centrifugal pump according to claim 2, wherein
said contact surface has a substantially curvilinear extension.

* * * * *